(12) United States Patent
Wuh et al.

(10) Patent No.: US 6,544,563 B2
(45) Date of Patent: *Apr. 8, 2003

(54) METHOD AND COMPOSITION FOR IMPROVING SEXUAL FITNESS

(75) Inventors: Hank C. K. Wuh, Los Altos, CA (US); Aileen S. Trant, Mountain View, CA (US)

(73) Assignee: The Daily Wellness Company, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/117,171

(22) Filed: Apr. 8, 2002

(65) Prior Publication Data

US 2002/0155181 A1 Oct. 24, 2002

Related U.S. Application Data

(63) Continuation of application No. 09/410,446, filed on Oct. 1, 1999, now Pat. No. 6,368,640, which is a continuation-in-part of application No. PCT/US99/07427, filed on Apr. 2, 1999.
(60) Provisional application No. 60/080,009, filed on Apr. 3, 1998, and provisional application No. 60/093,164, filed on Jul. 17, 1998.

(51) Int. Cl.$^7$ .............................................. A61K 35/78
(52) U.S. Cl. ...................... 424/728; 424/752; 424/774; 424/725
(58) Field of Search ................................ 424/725, 752, 424/728, 774, 451; 514/783

(56) References Cited

U.S. PATENT DOCUMENTS

| | | |
|---|---|---|
| 3,970,750 A | 7/1976 | Brockmeyer et al. |
| 4,154,813 A | 5/1979 | Kleinberg |
| 4,340,592 A | 7/1982 | Adibi |
| 4,388,325 A | 6/1983 | Orzalesi |
| 4,599,232 A | 7/1986 | Bertelli |
| 4,920,098 A | 4/1990 | Cotter et al. |
| 4,954,526 A | 9/1990 | Keefer |
| 5,032,608 A | 7/1991 | Dudrick |
| 5,034,377 A | 7/1991 | Adibi et al. |
| 5,106,836 A | 4/1992 | Clemens et al. |
| 5,157,022 A | 10/1992 | Barbul |
| 5,171,217 A | 12/1992 | March et al. |
| 5,217,997 A | 6/1993 | Levere et al. |
| 5,278,189 A | 1/1994 | Rath et al. |
| 5,364,644 A | 11/1994 | Walaszek et al. |
| 5,385,937 A | 1/1995 | Stamler et al. |
| 5,411,956 A | 5/1995 | Miyazaki et al. |
| 5,428,070 A | 6/1995 | Cooke et al. |
| 5,439,938 A | 8/1995 | Snyder et al. |
| 5,464,644 A | 11/1995 | Wullschlager et al. |
| 5,500,226 A | 3/1996 | Stroppolo et al. |
| 5,523,087 A | * 6/1996 | Shlyankevich ........... 424/195.1 |
| 5,543,430 A | 8/1996 | Kaesemeyer |
| 5,576,287 A | 11/1996 | Zaloga et al. |
| 5,576,351 A | 11/1996 | Yoshimura et al. |
| 5,594,032 A | 1/1997 | Gonzalez-Cadavid et al. |
| 5,626,883 A | 5/1997 | Paul |
| 5,631,031 A | 5/1997 | Meade |
| 5,650,418 A | 7/1997 | Rath et al. |
| 5,730,987 A | * 3/1998 | Omar ........................ 424/195.1 |
| 5,767,160 A | 6/1998 | Kaesemeyer |
| 5,780,039 A | 7/1998 | Greenberg et al. |
| 5,852,058 A | 12/1998 | Cooke et al. |
| 5,861,168 A | 1/1999 | Cooke et al. |
| 5,891,459 A | 4/1999 | Cooke et al. |
| 5,897,864 A | 4/1999 | Cohen |
| 5,945,452 A | 8/1999 | Cooke et al. |
| 5,977,073 A | 11/1999 | Khaled |
| 6,007,824 A | * 12/1999 | Duckett et al. .......... 424/195.1 |
| 6,117,872 A | 9/2000 | Maxwell et al. |

FOREIGN PATENT DOCUMENTS

| | | |
|---|---|---|
| EP | 0546796 | 6/1993 |
| JP | 58 55418 | 9/1981 |
| JP | 6 321786 | 5/1993 |
| JP | 5 163193 | 6/1993 |
| WO | WO 94/01006 | 1/1994 |

OTHER PUBLICATIONS

Balch et al. Prescription for Nutritional Healing; 2nd Edition, pp. 338–339, 1997.*

Product Alert: Source Naturals Dietary Supplement, Jan. 1998.*

Intimate Response: http://www.sourcenaturals.com/product-guide/guidepages/Intimate% 20Response.htm, Nov. 2000.*

McLeod, David; *Female infertility: a holistic approach*; Australian Journal of Medical Herbalism: vol. 8, No. 3; 1996; pp. 68–77.

Propping et al.; *Diagnostik und Therapie der Gelbkorperschache in der Praxis*; (in German/Summary in English); Therapiewoche, vol. 38, No. 41; 1988; pp. 2993–3001.

Moriyama et al.; *Studies on the usefulness of a long–term, high–dose treatment of methycobalamin for patients with oligozoospermia*; (in Janpanese/Summary in English); Japanese Journal dated 1987; pp. 151–156.

(List continued on next page.)

*Primary Examiner*—Christopher R. Tate
*Assistant Examiner*—Patricia D. Patten
(74) *Attorney, Agent, or Firm*—James Creighton Wray; Meera P. Narasimhan

(57) ABSTRACT

The invention provides methods and compositions for maintaining a state of wellness in a human by providing a dietary supplement comprising L-arginine, alone or in combination with ginseng and ginkgo biloba and/or additional nutritional supplements. The invention provides a unique blend of components that, in combination, synergistically bestow sexual wellness upon a human when taken regularly as a dietary supplement.

6 Claims, No Drawings

OTHER PUBLICATIONS

Netter et al.; *Effect of Zinc Administration on Plasma Testosterone, Dihydrotestosterone, and Sperm Count*; Archives of Andrology; vol. 7; 1981; pp. 69–73.

Czeizel, Andrew: *Periconceptional folic acid containing multivitamin supplementation*; European Journal of Obstetrics & Gynecology and Reproductive Biology, vol. 78, 1998; pp. 151–161.

Takihara et al.; *Zinc sulfate therapy for infertile male with or without vericocelectomy*; Urology, vol. XXIX, No. 6, Jun. 1987; pp. 638–641.

Internet Search Results, WebMD Health; Search Topics: "amino" amino acid: Branched–chain Amino Acids; Non-essential Amino Acids: Ginkgo: Ginseng: Protein in Diet: Want a Love Potion?; http://my.webmd.com; Jul. 23, 2001; 19 pages.

Internet Search Results, Auravita Health Channel; Search Topics: *Arginine: Asian Ginseng: Dehydroepiandrosterone(DHEA): Ginkgo biloba: Impotence*:www.auravita.com; Jul 23, 2001; 17 pages.

Kaplan et al.; *Safety and efficacy of sildenafil in postmenopausal women with sexual dysfunction*;; Urology, vol. 53, 1999; pp. 481–486.

Article Query, Pubmed medline; *Berman et al.; Effect of Estrogen withdrawal . . . (Urology, 1988 ): Goldstein et al., Vasculogenic female sexual dysfunction, (IntJImpotRes. 1998): Rosen et al., Effect of SSRIs on sexual function (JClin Psychopar, 1999): Pau et al., Dietary arginine . . . (JNutr. 1982)* (Abstracts).

Brown, Donald J.; *Vitex agnus castus Clinical Monograph*; Townsend Letter for Doctors and Patients; Oct. 1995, pp. 138–142.

Caan et al.; *Differences in Fertility Associated with Caffeinated Beverage Consumption*; American Journal of Public Health, vol. 88, No. 2, Feb. 1998; pp. 270–274.

Costa et al.; *L–carnitine in ideopathic asthenozoospermia: a multicenter study*; Andrologia, vol. 26, Jan. 1994; pp. 155–159.

Zheng et al.; *Effects of Ferulic Acid on Fertile and Asthenozoospermic Infertile Human Sperm Motility, Viability, Lipid Peroxidation, and Cyclic Nucleotides*; Free Radical Biology and Medicine, vol. 22, No. 4, Oct. 1995; pp. 825–831.

Kessopoulou et al,; *A double–blind randomized placebo cross–over controlled trial using the antioxidant vitamin E to treat reactive oxygen species associated male infertility*; Fertility and Sterility, vol. 64, No. 4, Oct. 1995: pp. 825–831.

Bayer, R.; *Treatment of Infertility and Vitamin E*; International Journal of Fertility, vol. 5, No. 1, Jan.–Mar. 1960: pp. 70–78.

Geva et al.; *The effect of antioxidant treatment on human spermatazoa and fertilization rate in an in–vitro fertilization program*; Fertility and Sterility, vol. 66, No. 3, Sep. 1996: pp. 430–434.

Dawson et al.; *Effect of ascorbic acid supplementation on the sperm quality of smokers*; Fertility and Sterility, vol. 58, No. 5, Nov. 1992: pp. 1034–1039.

Scott et al.; *The effect of oral supplementation on human sperm motility*; British Journal of Urology, vol. 82, 1998: pp. 76–80.

Hishikawa et al.; *Effect of Systemic L–Arginine Administration on Hemodynamics and Nitric Oxide Release in Man*; Japanes Heart Journal, Jan. 1992: pp. 41–48.

Internet Search Results, National Library of Medicine; Search Topics: *Vitamin B12 and oligospermia, Zinc sulphate and infertility, Zinc and Sperm Count, Folate and human fertility*; www.ncbi.nlm.nih.gov/entrez; Mar. 29, 2000—Apr. 5, 2000; 9 pages.

Moody, et al., "Effects of Long–Term Oral Administration of L–Arginne on the Rat Erectile Response," *The Journal of Urology*, vol. 158, pp. 942–947, Sep. 1997.

Zorgniotti, et al., "Effect of large doses of the nitric oxide precursor, L–arginine, on erectile dysfunction," *International Journal of Impotence Research*: Basic and clinical studies, 1994.

Database Prompt 'Online!,'The Gale Group, Product Alert May 9, 1994: "Golf Pro Nutrition Bar," Abstract.

Database WPI, Derwent Publications Ltd., Abstract of Patent CN1107349, Aug. 30,1995.

Auguet et al., "Bases Pharmacologiques de l'Impact Vasculaire de l'Extrait de Gingko biloba," *La Presse Medicale*, 15 (3) :1524–1528, 1986.

Chen et al., "Ginsenosides–Induced Nitric Oxide–Mediated Relaxation of the Rabbit Corpus Cavernosum," *British Journal of Pharmacology*, 115 : 15–18, 1995.

Ito et al., "The Effects of ArginMax, A Natural Dietary Supplement for Enhancement of Male Sexual Function," *Hawaii Medical Journal*, 57 : 741–744, 1998.

Nieri, "Evaluation Comparativa De Una Combination Terapeutica En Las Manifestaciones Clinicas Del Stress," *Pren. Med. Argent.*, 79 : 272–276, 1992.

Paick et al., "An Experimental Study of the Effect of Ginkgo Biloba Extract on the Human and Rabbit Corpus Cavernosum Tissue," *The Journal of Urology*, 156 : 1876–1880, 1996.

Rosen et al., "The International Index of Erectile Function (IIEF) : A Multidimensional Scale for Assessment of Erectile Dysfunction," *Urology*, 49 (6) : 822–830, 1997.

* cited by examiner

US 6,544,563 B2

METHOD AND COMPOSITION FOR IMPROVING SEXUAL FITNESS

CROSS-REFERENCES

This application is a continuation of application Ser. No. 09/410,446 filed Oct. 1, 1999, now U.S. Pat. No. 6,368,640 which is a continuation-in-part of PCT International Application No. PCT/US99/07427 filed Apr. 2, 1999, which claims priority of U.S. Provisional Application Nos. 60/080,009 filed Apr. 3, 1998 and 60/093,164 filed Jul. 17, 1998.

INTRODUCTION

1. Technical Field

This invention relates to the maintenance of a state of wellness in which sexual health is improved.

2. Background

Quality of life is increasingly valued in today's society. Proper nutrition and exercise, and healthy sexual function contribute to maintain an overall state of wellbeing, which can serve to manage stress, maintain a properly functioning immune system, protect against disease, maintain a positive mental outlook, and generally to enable one to feel good and enjoy life.

SUMMARY OF THE INVENTION

It has been found that the combination of L-arginine, ginseng, and optionally, ginkgo biloba when administered to a human in combination improves the blood circulation and improves the sexual, mental, and cardiac health of an individual. The invention provides methods and compositions for maintaining a state of wellness in an animal by providing a dietary supplement comprising L-arginine, in combination with ginseng and optionally ginkgo biloba and/or additional nutritional supplements. The invention provides a unique blend of components that, in combination, synergistically bestow sexual wellness upon an animal when taken regularly as a dietary supplement alone, or in combination with a pharmaceutical composition which facilitates smooth muscle relaxation and vascular dilatation.

One aspect of the invention is a composition for improving sexual fitness in an animal. The composition comprises (a) a metabolic precursor to nitric oxide. (b) a material for increasing nitric oxide synthase activity, and optionally (c) a material to promote vascular circulation, particularly microvascular circulation. Additional dietary supplements such as vitamins and minerals can also be included.

Another aspect of the invention is a method for improving sexual function in an animal. The method comprises administering the composition described above.

A third aspect of the invention is a method of treating sexual dysfunction in a male or female, e.g., erectile dysfunction in the male. The method comprises administering the composition described above.

Yet another aspect of the invention is a method for preparing a composition useful for improving sexual fitness. The process comprises combining the components of the composition described above, preferably into unit dosage forms.

A fifth aspect of the invention is an article of manufacture comprising the composition described above in combination with labeling that the composition is to be taken for sexual fitness.

DESCRIPTION OF SPECIFIC EMBODIMENTS

The compositions and methods of the invention provide a dietary supplement useful for maintaining a state of wellness in an animal, preferably a laboratory animal or domesticated animal, even more preferably a human, whether male or female.

The composition and method of the invention are particularly useful for improving sexual fitness in both males and females. The composition and method are particularly useful for people who want to remain sexually active as they grow older.

The composition of the invention comprises two, and preferably three, components: (a) a metabolic precursor to nitric oxide. (b) a material for increasing nitric oxide synthase activity, and optionally (c) a material to promote vascular circulation, particularly microvascular circulation. Preferably, the composition is a dietary supplement that is delivered over time to achieve the desired results.

A preferred dietary supplement of the invention comprises a combination of arginine, ginseng, and optionally ginkgo biloba, which is useful for improving blood flow and circulation. Improved blood flow is important for maintaining good sexual health. The compositions and methods of the invention improve sexual wellness without any undesirable side effects such as headache, nausea, gastric upset, chest pain, dizziness, vision disturbance, or change in blood pressure.

The Composition

The main component of the composition of this invention is a metabolic precursor to nitric oxide (NO), such as, for example, organic nitrates and nitrites and other compounds that are capable of conversion to nitric oxide. Many of such precursors are also called nitrovasodilators. Examples of organic nitrates include isoamyl nitrate, nitroglycerin, isosorbide dinitrate, erythrityl tetranitrate and pentaerythritol. Preferably, the precursor to NO is arginine. Arginine is an essential amino acid having the chemical name 2-amino-5-guanidinovaleric acid. It is preferably used in the physiologically active form which is designated as the "L" form. The compound is readily available from various sources in the commercial market place such as from Sigma Chemical Company or Aldrich Chemical Company in a pharmaceutical grade. It generally is available as a powder that generally is associated with two moles of water and forms monoclinic plates. Preferably the L-arginine in the composition is free of other amino acids, peptides and proteins that would interfere with the uptake of L-arginine into the animal's system.

The second component present in the composition is a material that increases nitric oxide synthase (NOS) activity. The increase in NOS activity may result from the increase in the quantity of NOS in the system or from an improverhent in the level of activity of NOS or by some other manner. A preferred material is ginseng. Ginseng is material extracted from the root of a plant that is a member of the ginseng family (Araliaceae), genus Panax. Ginseng plants grow in Asia and North America. *P. ginseng* grows in Northern China (Chinese ginseng) and Korea (Korean ginseng). The material extracted from the root is referred to as white ginseng or red ginseng. The former is dried *P. ginseng* root, while the latter is *P. ginseng* root steamed in caramel. American ginseng (*P. quinquefolium*) generally grows in the northern U.S. and Canada. Other relatives include Japanese ginseng (*P. japonicum*), San-Chi ginseng (*P. notoginseng*), Himalayan ginseng (*P. pseudoginseng*, ssp. *himalaicus* var *argustifolius*), and Siberian ginseng (*Eleutherococcus senticosus*).

The ginseng component in the composition is usually standardized ginseng obtained from plants originating from one or more geographical areas, and comprises, in total, about 1% to about 50% ginsenosides, preferably about 10% to about 35% ginsenosides, more preferably about 15% to about 20% ginsenosides, most preferably about 17.5% ginsenosides. Preferably the ginseng component comprises American ginseng and Korean ginseng. The American ginseng comprises about 1% to about 50% ginsenosides, preferably about 1% to about 10% ginsenosides, more preferably about 5% ginsenosides. The Korean ginseng comprises about 1% to about 50% ginsenosides, preferably about 10% to about 40% ginsenosides, more preferably about 30% ginsenosides. The ginseng component in a liquid or tonic is usually one or more extracts of ginseng from various geographical areas having a ratio of herb to solvent when extracted of about 1:2 to about 1:10, preferably about 1:5.

The various types of ginseng are available on the commercial market and are available from various sources, such as, for example, East Earth Herb and Natural Sourcing Solutions, Inc. The types and relative abundance of the chemical constituents of ginseng depend on the species, the part of the plant, the place of origin, the method of cultivation, and the technique of extraction used to obtain the ginseng. Different types of ginseng may have slightly different constituent profiles, but the type of ginseng used in this composition will be the material extracted from *Panax ginseng* or *Panax quinquefolius*. Preferably a mixture of American ginseng and Korean ginseng is employed.

The composition of the ginseng extracted from the roots of the various plants is quite similar among the different species used. Generally the ginseng will contain typical ginsenosides. A further discussion of the constituents of the various types of ginseng may be found in the American Chemical Society publication entitled "Folk Medicine: The Art and the Science," edited by Richard P. Steiner, University of Utah (1986).

Preferably, the composition of this invention also comprises a material that promotes vascular circulation in the person receiving the composition. This material may be a pharmaceutical or a dietary supplement or herb. Some materials that promote vascular circulation are known as vasodilators, e.g., hydralazine, minoxidil. sodium nitroprusside, diazoxide, phentolamine mesylate, phentolamine hydrochloride. phenoxybenzamine, yohimbine, nitroglycerine, thymoxamine, imipramine, isoxsuprine, naftidrofuryl, tolazoline, papaverine, and calcium channel blockers that act as vasodilators, such as nifedipine, nicardipine, nimodipine, verapamil and diltiazem. A particularly preferred material that promotes vascular circulation is Ginkgo biloba. Ginkgo biloba is extracted from the leaves of the ginkgo biloba tree. The leaves are harvested in late summer when the leaves have the highest level of active compounds. The extract is semipurified to remove undesirable compounds which do not contribute to the desired health benefits. The material can be highly concentrated and standardized to a known and consistent level of the active principals known as ginkgolides. Ginkgo biloba is readily available from the various sources throughout the herbal medicine industry, such as, for example, East Earth Herb and Natural Sourcing Solutions, Inc.

The ginkgo component in the composition as a solid, e.g., a tablet, capsule, or powder, is usually standardized ginkgo and comprises about 1% to about 50% flavone glycosides, preferably about 15% to about 30% flavone glycosides, more preferably about 24% flavone glycosides, and about 1% to about 20% terpene lactones, preferably about 5% to about 10% terpene lactones, more preferably about 6% terpene lactones. The ginkgo component in a liquid or tonic is usually an extract having a ratio of herb to solvent when extracted of about 1:2 to about 1:5, preferably about 1:2.

A dietary supplement composition comprising the combination of L-arginine, ginseng, and ginkgo biloba is administered to a subject orally as a capsule, tablet, powder or as an aqueous composition. If administered as a capsule, tablet, or powder, an amount of each of the three constituents is mixed in accordance with standard pharmaceutical practice to form a unit dosage that can be swallowed by taking water with the unit dosage. (See, for example, "Remington, The Science and Practice of Pharmacy," Nineteenth Edition, Mack Publishing co. for a discussion of the preparation of tablets and capsules/chapters 91–93). In general, the size of the tablet or capsule will be less than about a gram to maximize the ease of swallowing. In addition to the three major components of the composition of this invention, a dietary supplement also may contain antioxidant vitamins, vitamin-B-complex, and certain minerals. These additional constituents may be present in an amount up to about 100% of the daily values for each constituent for a male or female. By "daily values" is meant the Reference Daily Intake (RDI) as defined in 21 CFR §101.9(c)(8)(iv). Antioxidant vitamins include vitamins A (preferably as palmitate), C (preferably as ascorbic acid) and E (preferably as dl α tocopherol acetate). Vitamin-B complex includes thiamin (preferably as the mononitrate), riboflavin, niacin (preferably is niacinamide), vitamin B-6 (preferably as pyroxidine HCl), folate (preferable as folic acid), vitamin B-12 (preferably as cyanocobalamin), biotin, and pantothenic acid (preferably as calcium pantothenate). Minerals include zinc (preferably as zinc gluconate), calcium (preferably as calcium carbonate, iron (as iron gluconate), and selenium (preferably as sodium selenate).

Where a dietary supplement of this invention is administered in tablet, capsule, or powder form, the daily dosage can be administered in single or multiple unit dosages, preferably 1 to 10 unit dosages, more preferably 4–6 unit dosages. The constituents are combined to form a unit dosage in accordance with the amounts set forth in Table I, in which the broad, preferred, and more preferred range is are set forth as milligrams (mg) or % Daily Values.

TABLE I

| Constituent | Broad | Preferred | More Preferred |
|---|---|---|---|
| Arginine | 200–750 mg | 300–600 mg | 450–550 mg |
| Ginseng | 10–50 mg | 15–40 mg | 15–35 mg |
| Ginkgo biloba | 0–15 mg | 5–10 mg | 5–10 mg |
| Antioxidant vitamins | 0–100% | 5–50% | 10–20% |
| B-complex | 0–100% | 5–50% | 10–20% |
| Minerals | 0–100% | 5–30% | 10–20% |

A composition of this invention can be specifically tailored for either men or women. For example, a composition for men can have about 250 mg to about 750 mg arginine and about 15 mg to about 50 mg ginseng, preferably about 300 mg to about 600 mg arginine and about 20 mg to about 40 mg ginseng, whereas a composition for women can have about 200 mg to about 600 mg arginine and about 10 mg to about 25 mg ginseng, preferably about 300 mg to about 500 mg arginine and about 15 mg to about 20 mg ginseng. As another example, a composition for a man can comprise American ginseng and Korean ginseng, whereas a composition for a woman can comprise Korean ginseng but not American ginseng. In addition, a composition for a man may have a higher percentage of zinc and selenium, whereas a composition for a woman may have a higher percentage of calcium and iron. Furthermore, the composition can further comprise about 0 mg to about 50 mg damiana, preferably about 5 mg to about 15 mg, particularly for a composition for a woman.

Where the dietary supplement of this invention is an aqueous composition, it may be administered as single or multiple drinks having a volume of up to 500 milliliters (ml) or more. Preferably however it is prepared as a drink having a volume of about 50 to about 300 ml with appropriate flavoring to be consumed either as a cold or hot beverage. Preferably it is flavored with a sweetener and a flavoring agents for easier consumption. A daily dose of two drinks each of about 100 ml has been found to be particularly useful. Table II sets forth the broad, preferred, and most preferred amounts in which the constituents are combined to form a unit dosage of 100 ml.

TABLE II

| Constituent | Broad | Preferred | More Preferred |
|---|---|---|---|
| Arginine | 400–10000 mg | 750–3000 mg | 1000–2000 mg |
| Ginseng | 15–600 mg | 25–400 mg | 50–200 mg |
| GBE | 0–300 mg | 10–250 mg | 25–100 mg |
| Antioxidant vitamins | 0–200% | 25–150% | 50–100% |
| B-complex | 0–200% | 25–150% | 50–100% |
| Minerals | 0–100% | 25–100% | 50–100% |

A preferred composition for a man comprises about 500 to about 10000 mg arginine and about 25 to about 600 mg ginseng, preferably about 100 to about 400 mg ginseng, most preferably about 150 to about 250 mg ginseng.

It should be appreciated that some vitamins and minerals, particularly some of the fat soluble vitamins, zinc, and selenium can be harmful in large doses. Thus, preferably the daily dosage of such vitamins and minerals should not exceed 200% Daily Values. If present, preferred daily dosages of the preferred minerals include about 15–30 mg zinc and about 70 mcg to about 140 mcg selenium. Preferred daily dosages of the preferred vitamin antioxidants include about 5000 IU to about 10000 IU Vitamin A, about 60 mg to about 120 mg Vitamin C, and about 30 IU to about 60 IU Vitamin E. Preferred daily dosages of the preferred B-vitamins include about 1.5 mg to about 3 mg thiamin, about 1.7 mg to about 3.4 mg riboflavin, about 2 mg to about 4 mg Vitamin B-6, and about 6 mcg to about 12 mcg Vitamin B-12. Preferred dosages of some other preferred vitamins include about 20 mg to about 40 mg niacin, about 400 mcg to about 800 mcg folate, about 300 mcg to about 600 mcg biotin, and about 10 mg to about 20 mg pantothenic acid.

The dietary supplement can be administered in tablet, capsule, liquid, powder, nutritional bar or effervescent form. Methods of preparation of formulations for various forms of administration are known in the art and discussed in detail in *Remington's Pharmaceutical Sciences*, Eighteenth Edition (1990), incorporated herein by reference. Tablets, for example, can include components in addition to the active ingredients, such as diluents, binders, lubricants, glidants, disintegrants, coloring agents, and flavoring agents. Capsules, for example, are made largely from gelatin, FD&C colorants, and sometimes an opacifying agent such as titanium dioxide. Effervescent tablets, for example, comprise in addition to the active ingredients, sodium bicarbonate and an organic acid such as tartaric acid or citric acid. In the presence of water, these additives react, liberating carbon dioxide as a result of an acid-base reaction, which acts as a disintegrator and produces effervescence. Concentrations of the additives vary according to the acidic or basic nature of the active ingredients in order to ensure that an acid-base reaction occur upon contact of the effervescent tablet with water. The dietary supplement can also be formulated as a powder, which can be ingested directly or which can be ingested after reconstitution with an aqueous liquid. Preferably the supplement is administered in a capsule, effervescent tablet, or as a liquid tonic. The formulations can also comprise a flavoring agent.

Method of Administration

Another aspect of this invention is a method for improving sexual fitness in an animal, particularly human subject. The method comprises administering as unit dosage a composition of the invention, e.g., as a dietary supplement comprising the combination of L-Arginine, ginseng, and optionally ginkgo biloba.

The regular administration of the composition over time results in improved sexual fitness, i.e., sexual function, in both males and females. Sexual fitness is determined by providing a subject taking the composition with a sexual function questionnaire. For women, the questionnaire follows the *Index of Female Sexual Function* (IFSF). This is a 9-item, self-administered questionnaire. (See *Urology* 53: 481–486, 1999.) The questionnaire is directed at the level of discomfort during intercourse, the degree of vaginal dryness, the number of attempts at sexual intercourse, the rate and level of sexual desire, the level of satisfaction with a woman's sex life and relationship, the degree of clitoral sensation during sexual stimulation and the quality of orgasm. In general, the administration of a composition of this invention results in improved sexual fitness as measured by one or more of the factors in the IFSF, e.g., increased clitoral sensation and improved sexual desire.

For men, the improvement in sexual fitness is determined by administering the *International Index of Erectile Function* (IIEF), a 15-question, validated, multidimensional, self-administered questionnaire. (See *Urology:* 49, 822–830.) The questionnaire is directed at determining the ability to obtain an erection, the hardness of an erection, ability to penetrate a partner and maintain the erection, satisfaction level of intercourse, ability to ejaculate and experience orgasm, level of sexual desire, level of satisfaction with sex life and sexual relationship with a partner. In general, the administration of a composition of this invention over time in accordance with the method of the invention results in improved sexual fitness as measured by one or more of the factors in the IIEF, e.g., improved ability to achieve an erection, an erection that can be maintained for a period of time that is longer than would occur without the administration of the dietary supplement, improvement in the quality of the orgasm for the subject. In addition, it is found that upon exertion by any significant exercise the subject's breathing and ability to breathe is improved.

It is believed that the dietary supplement increases the production of nitric oxide (NO) by providing more substrate (L-arginine) for its production and upregulating the activity of nitric oxide synthase (NOS), the enzyme that cleaves L-arginine to form NO. NO in turn signals the creation of cGMP which triggers an erection in men. The dietary supplement helps improve the body's production of cGMP. It is believed that female sexual function is accomplished physiologically in a similar manner. For example, cGMP triggers lubrication and engorgement of the clitoral tissue. Thus, the dietary supplement of the invention is useful for improving sexual wellness, in both men and women. The dietary supplement can also be used in a method of medical treatment, such as, for example, the treatment of sexual dysfunction, or for the preparation of a medicament for such treatment.

As shown in Example 7, simultaneous usage of Viagra™ (sildenafil citrate) and a dietary supplement comprising L-arginine, ginseng and ginkgo biloba improves sexual function in patients who did not respond satisfactorily to Viagra™ alone. Viagra™, which is currently prescribed in 25, 50 and 100 mg dosages for erectile dysfunction, exerts its effects by transiently inhibiting PDE5, a chemical in the body responsible for the degradation of cGMP in the corpus cavernosum (penis cavity). In essence, Viagra™ decreases the body's ability to breakdown cGMP for a short time, allowing more of it to accumulate. The resulting higher levels of cGMP increases the ease in achieving and maintaining an erection.

Alprostadil is a smooth muscle relaxant. The binding of alprostadil to its receptors is accompanied by an increase in intracellular cAMP levels. Human cavernous smooth muscle cells respond to alprostadil by releasing intracellular calcium into the surrounding medium. Smooth muscle relaxation is associated with a reduction of the cytoplasmic free calcium concentration. Alprostadil also attenuates pre-synaptic noradrenaline release in the corpus cavernosum, which is essential for the maintenance of a flaccid and non-erect penis.

The dietary supplement, Viagra™, and alprostadil all work to facilitate smooth muscle relaxation and vascular dilatation. Thus. yet another aspect of this invention is a method for enhancing the response of a male subject to a pharmaceutical composition which facilitates smooth muscle relaxation and vascular dilatation, preferably which increases the levels of cGMP in the corpus cavernosum. The method is useful for subjects which have an unsatisfactory response to the pharmaceutical composition and wish to improve the efficacy of the pharmaceutical composition. The method comprises administering a daily dosage of a dietary supplement comprising, in at least one unit dosage, L-arginine, ginseng, and ginkgo biloba for a number of days sufficient to improve the ability of a male subject to achieve penile erection when the pharmaceutical composition is administered. Preferably the dietary supplement is administered for at least one day, more preferably at least about one week, and most preferably at least about two weeks. Other compounds which increase the levels of cGMP include, but are not limited to, alprostadil.

The invention also provides a method for reducing the pharmaceutically effective dose of a pharmaceutical composition, such as, e.g., a composition comprising sildenafil citrate and/or alprostadil, which facilitates smooth muscle relaxation and vascular dilatation, preferably which increases the levels of cGMP in the corpus cavemosum. The method is useful for subjects who, having experienced undesirable side effects with their current dosage of the pharmaceutical composition, wish to reduce the dosage to avoid the side effects yet maintain a favorable level of efficacy. The method is also useful for subjects who do not have problems with side effects from the current dosage of the pharmaceutical composition but wish to achieve the same level of efficacy with a reduced dosage for reasons of cost, preference for natural products, etc. The method comprises administering, to a male subject being treated with a first dosage of the pharmaceutical composition, a daily dosage of a dietary supplement comprising, in at least one unit dosage, L-arginine, ginseng, and ginkgo biloba for a time sufficient to enhance the effects on said cGMP levels mediated by a first dosage of a pharmaceutical composition prescribed for erectile dysfunction; and adjusting said first dosage to a second dosage which exerts the same effects on said cGMP levels of said first dosage prior to commencement of said daily dosage of said dietary supplement.

Another preferred aspect of the invention is a method of ameliorating erectile dysfunction, comprising administering a daily dosage of a dietary supplement comprising L-arginine, ginseng, and ginkgo biloba and administering, when an erection is desired, a pharmaceutical composition, such as, e.g., a composition comprising sildenafil citrate and/or alprostadil, which facilitates smooth muscle relaxation and vascular dilatation, preferably which increases the levels of cGMP in the corpus cavernosum. Typically, the pharmaceutical composition is administered less than about 6 hours before attempting intercourse, preferably from about 4 hours to about 0.5 hour before sexual activity, and most preferably about 1 hour before sexual activity. Preferred dosages of the pharmaceutical composition are about one fourth of the dosages normally prescribed, preferably about one half of the normal dosages. For example, preferred dosages of sildenafil citrate for this method include, but are not limited to, about 6.25 mg, 12.5 mg, 25 mg, and 50 mg dosages.

In general, the administration of the composition of this invention is carried out on a daily basis for a period of time sufficient to improve sexual fitness. The time and amount administered will vary from subject to subject and will be influenced by the age of the subject, whether male or female. Generally, the younger the subject, the sooner the results will be seen and the smaller the amount needed to see the results. As a subject ages, the composition will have to be administered over a longer period of time and in larger amounts for a subject to experience results. The composition is preferably administered for at least two days. More preferably it is administered for at least about a one week period, even more preferably at least about a two week period, and most preferably for at least about a four week period. By ingesting the composition over an extended period of time making the dietary supplement an addition to the diet on a sustained basis, sexual fitness will be improved generally. In administering the composition to an individual, the composition is administered in either the tablet, capsule or liquid form in accordance with the composition discussed herein before. Typically, a desired daily dosage is achieved by administering an appropriate quantity of unit dosages. Generally the amounts administered on a daily basis will be between about 500 mg—10000 mg of L-arginine per day, preferably about 2000 to 5000 mg of L-arginine a day. The ginseng is administered at a rate of about 25 mg to about 600 mg per day preferably about 100 to about 400 mg per day. The ginkgo biloba is administered at a rate of about 8 mg to 300 mg per day, preferably about 50 to about 250 mg per day. Optionally up to 200 percent of the daily values of antioxidant vitamins, vitamin B complex and certain minerals, as discussed hereinbefore, are administered along with the dietary supplement combination.

The supplement can be administered weekly or even monthly, but daily administration is preferred, preferably on an empty stomach. The daily dosage can be a single unit dosage or a multiple unit dosage. For example, a daily dosage can be from 1 to 10 capsules or 1 to 4 100 ml beverages daily. Preferably the daily dosage is 6 capsules or 2 100 ml beverages. Preferably the daily dosage is administered in two unit dosages, preferably upon waking and at bedtime. Some preferred dietary supplements are discussed further in Examples 1–3.

Another aspect of this invention is a method for preparing a composition useful for improving sexual fitness. The process comprises combining L-arginine with a material for increasing nitric acid synthase activity (e.g., ginseng) and optionally (a) a material that promotes vascular circulation (e.g., ginkgo biloba) and (b) additional dietary supplements such as vitamins and minerals. The mixture is formed into unit dosage forms and labeled as being useful for improving sexual fitness.

Still another aspect of this invention is an article of manufacture that is a composition in accordance with this invention in combination with labeling that the composition is to be taken for sexual fitness. The article is simply a container such as a bottle or box containing unit dosage forms (e.g., tablets, capsules) with labeling indicating the rate at which the unit dosage should be consumed, e.g., see Examples 1–3.

EXAMPLES

Example 1

Dietary Supplement in Gel Cap Form

The dietary supplement is provided in a 6 gel cap serving to be taken daily, preferably by a human male, for at least 2–3 weeks, preferably on an empty stomach, and comprises the following components per serving:

| | |
|---|---|
| Vitamin A | 5000 IU |
| Vitamin C | 60 mg |
| Vitamin E | 30 IU |
| Thiamin | 1.5 mg |
| Riboflavin | 1.7 mg |
| Niacin | 20 mg |
| Vitamin B-6 | 2 mg |
| Folate | 400 mcg |
| Vitamin B-12 | 6 mcg |
| Biotin | 300 mcg |
| Pantothenic acid | 10 mg |
| Zinc | 15 mg |
| Selenium | 70 mcg |
| L-arginine | 3000 mg |
| American Ginseng-standardized (5% ginsenosides) | 100 mg |
| Korean Ginseng-standardized (30% ginsenosides) | 100 mg |
| Ginkgo Biloba-standardized (24% flavone glycosides, 6% terpene lactones) | 50 mg |

Other ingredients: Rice Flour Powder Magnesium Stearate, Silica

Example 2

Dietary Supplement in Tonic Form

The dietary supplement is provided in two 100 ml servings to be taken daily, preferably by a human male, for at least 2–3 weeks, preferably on an empty stomach, and comprises the following components per serving:

| | |
|---|---|
| Vitamin A | 5000 IU |
| Vitamin C | 60 mg |
| Vitamin E | 30 IU |
| Thiamin | 1.5 mg |
| Riboflavin | 1.7 mg |
| Niacin | 20 mg |
| Vitamin B-6 | 2 mg |
| Folate | 400 mcg |
| Vitamin B-12 | 6 mcg |
| Biotin | 300 mcg |
| Pantothenic acid | 10 mg |
| Zinc | 7.5 mg |
| Selenium | 70 mcg |
| L-arginine | 1500 mg |
| American Ginseng-root (1:5) | 100 mg |
| Korean Ginseng-root (1:5) | 100 mg |
| Ginkgo Biloba-freshleaf (1:2) | 100 mg |

Other ingredients: Filtered Water, High Fructose Corn Syrup, Strawberry Concentrate, Citric Acid, Natural Flavors

Example 3

Dietary Supplement in Gel Cap Form

The dietary supplement is provided in a 6 gel cap serving to be taken daily, preferably by a human female, for at least 2–3 weeks, preferably on an empty stomach, and comprises the following components per serving:

| | |
|---|---|
| Vitamin A | 5000 IU |
| Vitamin C | 60 mg |
| Vitamin E | 30 IU |
| Thiamin | 1.5 mg |
| Riboflavin | 1.7 mg |
| Niacin | 20 mg |
| Vitamin B-6 | 2 mg |
| Folate | 400 mcg |
| Vitamin B-12 | 6 mcg |
| Biotin | 300 mcg |
| Pantothenic acid | 10 mg |
| Calcium | 500 mg |
| Iron | 9 mg |
| Zinc | 7.5 mg |
| L-arginine | 2500 mg |
| Korean Ginseng-standardized (30% ginsenosides) | 100 mg |
| Ginkgo Biloba-standardized (24% flavone glycosides, 6% terpene lactones) | 50 mg |
| Damiana leaves (Tumera Aphrodisiaca) | 50 mg |

Other ingredients: Rice Flour Powder, Magnesium Stearate, Silica

Example 4

Regular Administration of L-arginine to Maintain a State of Wellness Thereby Reducing the Likelihood of Developing a Headache A healthy man takes 3,000 mg L-arginine as a separate dietary supplement daily on an empty stomach for a minimum of 2–3 weeks.

Example 5

Regular Administration of L-arginine in Combination with Ginseng and Ginkgo Biloba to Maintain a State of Wellness 18 healthy men, age 29 to 44, were instructed to take two 100 ml servings of the dietary supplement described in Example 2 daily on an empty stomach for eight weeks. Survey data was collected before and after the men begin taking the dietary supplement. The volunteers noted a 29 to 33% increase in quality of orgasm, sexual confidence and sexual stamina. Penile hardness ratings and sexual enjoyment ratings increased by 13%. Ease of breathing after exertion also increased by 29%. Frequency of headaches decreased.

Example 6

Administration of L-arginine in Combination with Ginseng and Ginkgo Biloba in Men with Erectile Dysfunction Male subjects with mild to moderate erectile dysfunction were instructed on the use and regimen of the dietary supplement of Example 1 and were requested to fill out a baseline SFQ survey. Subjects started a twice-per-day regimen of the dietary supplement, once in the morning upon waking and once in the evening at bedtime. A 4-week supply of the dietary supplement was provided. After completing the 4-week regimen, patients were instructed to complete a 4-week SFQ survey and return to the test center for follow-up evaluation and examination.

The SFQ was used as the primary test instrument. The SFQ is a self-administered questionnaire beginning with the validated IIEF (International Index of Erectile Function used with permission) test instrument and including other validated test instruments designed to measure changes in erectile function, sexual function, and quality of life. (Rosen et al., Urology, June 1997, 49(6):822–830; Derogatis L R, J Sex Marital Ther, 1997, 23(4):291–304; Conte H R, Arch Sex Behav, December 1983, 12(6):555–576; Jenkinson et al., BMJ, May 29, 1993, 306(6890):1437–1440; Garrarr et al., BMJ, May 29, 1993, 306(6890):1440–1444) In addition, the SFQ included questions regarding subject's activities and condition during the trial period.

| Subject Group Profile at Baseline: | |
| --- | --- |
| Total # of subjects | 25 |
| Age range | 40–77 |
| # hypertensive | 19 |
| # diabetes mellitus | 4 |

Patient responses to SFQ survey questions at 4 weeks were compared to SFQ responses at baseline. A comparison analysis was performed for those subjects whose degree of erectile dysfunction were mild to moderate as characterized by a minimal baseline score of 2. For each SFQ variable, a comparison was made of those subjects who initially had a baseline score of at least 2 to their 4 week score on the same variable. The results were then pooled, summarized, and evaluated to reflect the percentage of subjects with improvement in each of the SFQ question variables. 88.9% of subjects showed improvement in the ability to maintain erection during intercourse. 75.0% of subjects showed improvement in satisfaction with overall sex life. 20.0% of subjects showed improvement in number of orgasms. 12.5% of subjects showed improvement in the number of times attempted intercourse.

There were no significant changes in blood pressure or other significant side effects as noted by net % of patients reporting increase or decrease as follows:

| | |
| --- | --- |
| Headaches: | −4.8% |
| Nausea: | −4.8% |
| Stomach upset: | −14.3% |
| Chest pain: | 0% |
| Dizziness: | 0% |
| Vision disturbance: | 0% |

Example 7

Administration of L-arginine in Combination with Ginseng and Ginkgo Biloba in Patients that had not Responded Satisfactorily to Viagra™

Six patients which had not responded satisfactorily to Viagra™ (sildenafil citrate) were asked to use the dietary supplement of Example 1 for 4 weeks on a daily basis and to try Viagra™ again as they felt the need. Typically patients used Viagra™ about 1 hour prior to engaging in sexual activity. Patients were using either 50 or 100 mg dosages of Viagra™. 4 out of 6 showed dramatic improvement based on an increase in several key IIEF variables, such as erection frequency, erection firmness, penetration ability, maintenance frequency, and maintenance ability.

Example 8

Female Clinical Study Regarding Sexual Fitness

A double-blind, placebo-controlled study was carried out examining the role of dietary supplementation in female sexual function. A composition of Example 3 was given to thirty-nine (39) participants, ages 22–61 years. All individuals were experiencing some degree of sexual dysfunction. Evaluations were conducted using the Female Sexual Function Index (FSFI), a validated instrument used for the evaluation of sildenafil (Viagra) in women. Of the 39 participants, sixteen (16) received the composition and twenty-three (23) received placebo. At week four, 62.5% of women in the active group experienced improvement in clitoral sensation during sexual stimulation compared to 39.1% in the placebo group. In the active group, 68.8% experienced improvement in their level of sexual desire compared to 43.5% in the placebo group p=0.06. No headache, nausea, vomiting, stomach upset, visual disturbance, hypotension, dizziness or other complaints were noted in either group.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition for improving sexual fitness in an animal, comprising:
 (a) about 3000 mg L-arginine,
 (b) about 100 mg American ginseng (5% ginsenosides),
 (c) about 100 mg panax ginseng (30% ginsenosides),
 (d) about 50 mg ginkgo biloba (24% flavone glycosides),
 (e) about 50 mg damiana (turnera aphrodisiaca),
 (f) about 5000 IU vitamin A (as palmitate),
 (g) about 60 mg vitamin C (as ascorbic acid),
 (h) about 30 IU vitamin E (as d-alpha-tocopherol),
 (i) about 1.5 mg thiamin (as thiamin mononitrate),
 (j) about 1.7 mg riboflavin,
 (k) about 20 mg niacin (as niacinamide),
 (l) about 2 mg vitamin B6 (as pyridoxine hydrochloride),
 (m) about 400 mcg folate (as folic acid),
 (n) about 6 mcg vitamin B12 (as cyanocobalamin),
 (o) about 300 mcg biotin,
 (p) about 10 mg pantothenic acid (as calcium pantothenate),
 (q) about 500 mg calcium (as carbonate),
 (r) about 9 mg iron (as gluconate),
 (s) about 15 mg zinc (as gluconate), and
 (t) about 70 mcg selenium (as sodium selenate).

2. The composition of claim 1, wherein said animal is a human.

3. The composition of claim 2, wherein said human is a man.

4. A composition for improving sexual fitness in an animal, comprising:
   (a) about 2500 mg L-arginine,
   (b) about 100 mg American ginseng (5% ginsenosides),
   (c) about 100 mg panax ginseng (30% ginsenosides),
   (d) about 50 mg ginkgo biloba (24% flavone glycosides),
   (e) about 50 mg damiana (turnera aphrodisiaca),
   (f) about 5000 TU vitamin A (as palmitate),
   (g) about 60 mg vitamin C (as ascorbic acid),
   (h) about 30 IU vitamin E (as d-alpha-tocopherol),
   (i) about 1.5 mg thiamin (as thiamin mononitrate),
   (j) about 1.7 mg riboflavin,
   (k) about 20 mg niacin (as niacinamide),
   (l) about 2 mg vitamin B6 (as pyridoxine hydrochloride),
   (m) about 400 mcg folate (as folic acid),
   (n) about 6 mcg vitamin B12 (as cyanocobalamin),
   (o) about 300 mcg biotin,
   (p) about 10 mg pantothenic acid (as calcium pantothenate),
   (q) about 500 mg calcium (as carbonate),
   (r) about 9 mg iron (as gluconate),
   (s) about 7.5 mg zinc (as gluconate), and
   (t) about 70 mcg selenium (as sodium selenate).

5. The composition of claim 4, wherein said animal is a human.

6. The composition of claim 5, wherein said human is a woman.

* * * * *